United States Patent [19]
Biedermann et al.

[11] Patent Number: 5,644,140
[45] Date of Patent: Jul. 1, 1997

[54] APPARATUS FOR CHECKING SEMICONDUCTOR WAFERS WITH COMPLEMENTARY LIGHT SOURCES AND TWO CAMERAS

[75] Inventors: Ernst Biedermann, Regensburg; Manfred Ben El Mekki, Fürstenfeldbruck; Kenneth Weisheit, Augsburg; Thomas Griebsch; Gerhard Ross, both of München, all of Germany

[73] Assignee: Siemens Aktiengesellschaft, Munich, Germany

[21] Appl. No.: 425,824

[22] Filed: Apr. 20, 1995

[30] Foreign Application Priority Data

Apr. 20, 1994 [DE] Germany ............... 44 13 832.6

[51] Int. Cl.⁶ ................................................ G01N 21/86
[52] U.S. Cl. .................... 250/559.08; 250/239; 356/237
[58] Field of Search ................... 250/559.45, 559.4, 250/559.08, 559.42, 559.44, 559.46, 239; 356/237, 446, 426; 414/939, 935, 937

[56] References Cited

U.S. PATENT DOCUMENTS

| 4,876,455 | 10/1989 | Sanderson et al. ............ 250/559.4 |
| 4,929,081 | 5/1990 | Yamamoto et al. ............ 356/354 |
| 5,172,005 | 12/1992 | Cochran et al. ............ 250/559.08 |
| 5,302,836 | 4/1994 | Siu ............ 356/237 |

FOREIGN PATENT DOCUMENTS

| 0159354 | 4/1987 | European Pat. Off. . |
| 3806209 | 9/1988 | Germany . |
| 4003983 | 8/1991 | Germany . |
| 4032327 | 7/1992 | Germany . |

*Primary Examiner*—Que Le
*Attorney, Agent, or Firm*—Herbert L. Lerner; Laurence A. Greenberg

[57] ABSTRACT

One embodiment of an apparatus for checking semiconductor wafers includes a receiver for a semiconductor wafer to be checked. A light illuminates the wafer. A hemispherical hood has a surface and a hemispherical region defining an interior inside the hemispherical region. A further hood is disposed in the vicinity of the light. A camera is disposed at the hemispherical hood and has a lens looking into the interior inside the hemispherical hood. A evaluator is connected to the camera for controlling the camera and receiving, buffer-storing, processing and outputting data transmitted by the camera. Another embodiment includes a first light directly illuminates the wafer with light of a first color and a second light indirectly illuminates the wafer with light of a second color being complementary to the first color. A surface of the hood is of the second color. The further hood is opaque to incident light, permitting the wafer to be illuminated directly by the first light, and permitting the wafer to only be illuminated indirectly by the second light. A first camera has a filter admitting only light of the first color and a second camera has a filter admitting only light of the second color and being disposed at an angle greater than 0° relative to a center point of the receiver for the semiconductor wafer to be checked.

11 Claims, 3 Drawing Sheets

APPARATUS FOR CHECKING SEMICONDUCTOR WAFERS WITH COMPLEMENTARY LIGHT SOURCES AND TWO CAMERAS

BACKGROUND OF THE INVENTION

1. Field of the Invention

The invention relates to an apparatus for checking semiconductor wafers.

In the production of integrated semiconductor circuits, the semiconductor wafers must be repeatedly checked for the proper characteristics. Defective semiconductor wafers need to be detected in the process, so that they can either be eliminated from the further course of production entirely or be suitably reworked before further production steps are performed on them and they are then returned to the normal course of production, on the condition that they are free of defects.

Checks of semiconductor wafers for perfect characteristics (for instance checking for freedom from particles, or in other words soil and deposits, checking for paint coatings applied, etc.) are known to be eminently important if good yields in the production process are to be attained.

Heretofore, such checks have been done manually, either with the aid of conventional microscopes or without a microscope, with oblique light. On one hand, that is very tiring for the worker, especially for his or her eyes and back (because of posture and long hours of sitting). On the other hand, it involves major uncertainties as well, since the worker's concentration on detecting defects and sorting out good and bad wafers diminishes over time.

2. Summary of the Invention

It is accordingly an object of the invention to provide an apparatus for checking semiconductor wafers, which overcomes the hereinafore-mentioned disadvantages of the heretofore-known apparatuses of this general type and with the aid of which a checking process can be automated.

With the foregoing and other objects in view there is provided, in accordance with the invention, an apparatus for checking semiconductor wafers comprising a receiver for a semiconductor wafer to be checked; a light for illuminating the semiconductor wafer; a hemispherical hood having a surface and a hemispherical region defining an interior inside the hemispherical region; a further hood disposed in the vicinity of the light; a camera being disposed at the hemispherical hood and having a lens looking into the interior inside the hemispherical hood; and an evaluator being connected to the camera for controlling the camera and receiving, buffer-storing, processing and outputing data transmitted by the camera.

With the objects of the invention in view, there is also provided an apparatus for checking semiconductor wafers, comprising a receiver for a semiconductor wafer to be checked, the receiver having a center point; a first light for directly illuminating the semiconductor wafer with light of a first color; a second light for indirectly illuminating the semiconductor wafer with light of a second color being complementary to the first color; a hemispherical hood having a surface of the second color and having a hemispherical region defining an interior inside the hemispherical region; a further hood being disposed above the first light, being opaque to incident light, permitting the semiconductor wafer to be illuminated directly by the first light, and permitting the semiconductor wafer to only be illuminated indirectly by the second light; a first camera disposed at the hemispherical hood vertically above the center point of the receiver for the semiconductor wafer to be checked, the first camera having a lens looking into the interior and a filter admitting only light of the first color; a second camera being disposed at the hemispherical hood and having a lens looking into the interior and a filter admitting only light of the second color, the second camera being disposed at an angle greater than 0° relative to the center point of the receiver for the semiconductor wafer to be checked; and an evaluator being connected to both of the cameras for controlling the cameras and for receiving, buffer-storing, further processing and outputting data transmitted from the cameras.

Other features which are considered as characteristic for the invention are set forth in the appended claims.

Although the invention is illustrated and described herein as embodied in an apparatus for checking semiconductor wafers, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE PREFERRED EMBODIMENTS

Figure 1:
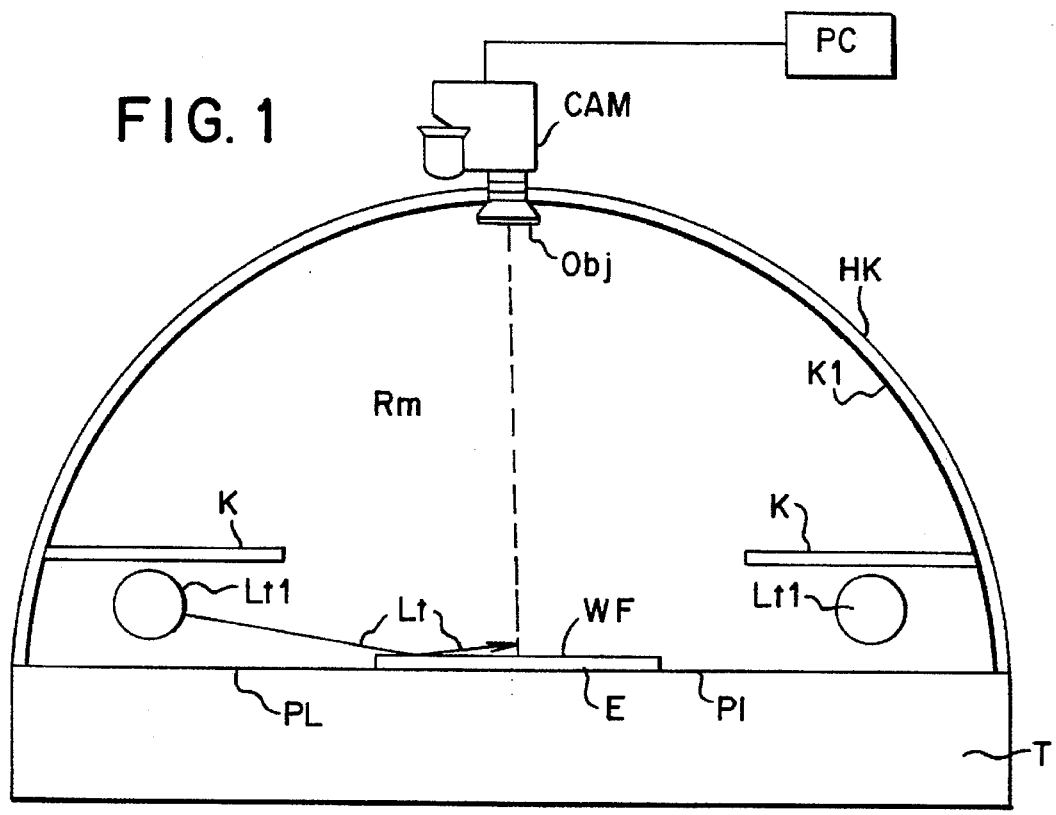
FIGS. 1–3 are diagrammatic, side-elevational views of advantageous embodiments of the apparatus according to the invention.

Referring now to the figures of the drawing in detail and first, particularly, to FIG. 1 thereof, it is seen that a first embodiment of the apparatus according to the invention may be disposed on a table T, for example (as is also true for the other two embodiments of FIGS. 2 and 3), or on some other suitable support that stands firmly. The apparatus has a receiver or a device E for receiving a semiconductor wafer WF to be checked, and a bottom plate P1, although that is not absolutely necessary. The device E may be a component of the bottom plate P1. However, in other embodiments of the apparatus according to the invention, it may alternatively be disposed on or let into the bottom plate P1. The apparatus also has a hemispherical hood device or hood HK with an interior Rm, which is largely closed off by the bottom plate P1.

Inside the closed-off space Rm is a preferably, but not absolutely necessarily, annular light or lighting device Lt1, which serves to provide direct illumination of the semiconductor wafer WF. The annular embodiment enables uniform illumination of the semiconductor wafer WF. Inside the closed-off space Rm, the hemispherical hood device HK has a surface K1, which absorbs incident light Lt.

Disposed above the lighting device Lt1 is a further hood device or hood K, which absorbs incident light Lt. The further hood device K is constructed in such a way that the semiconductor wafer WF can be illuminated directly by the lighting device Lt1, while the hemispherical hood HK is for the most part shielded from the direct light of the lighting device Lt1. Due to these requirements, it is advantageous, especially if there is an annular construction of the lighting device Lt1, for the further hood device K to be annular as well.

A camera CAM is disposed vertically above a center point of the device E for receiving the wafer WF to be checked. The camera CAM is disposed on the hemispherical hood device HK in such a way that a lens Obj looks into the closed-off space Rm, particularly at the point where the semiconductor wafer WF to be checked is located during operation. The camera CAM may be disposed in such a way that its lens Obj protrudes into the closed-off space Rm, as is shown in FIG. 1, or else in such a way that an edge of its lens Obj is approximately flush with the hemispherical hood HK.

The camera CAM is connected to an evaluator or evaluation device PC, which serves to control the camera and to receive, buffer-store, process and output data transmitted from the camera CAM. These data may be transmitted in analog form (in the form of "pictures") or in digital form, if the camera CAM is already equipped for digital transmission (for instance, if it has A/D converters). The evaluation device PC is typically a computer, for instance a personal computer or a data processing system. However, it is also conceivable for it to be constructed solely with hardware dedicated to a suitable method.

The following features of the apparatus are advantageous:

The surface K1 of the hemispherical hood HK that absorbs the light Lt is black.

The light Lt output by the lighting device Lt1 is white.

The further hood device K has a black surface.

The surface of the bottom plate P1 is black on its side facing toward the hemispherical hood device HK.

If other parts of the camera CAM are located inside the closed-off space Rm, then they are disposed in such a way that from the standpoint of the semiconductor wafer WF to be checked, they are concealed by the lens Obj.

The process of checking can be automated by means of this embodiment, for instance with the aid of the method described below.

Figure 5:
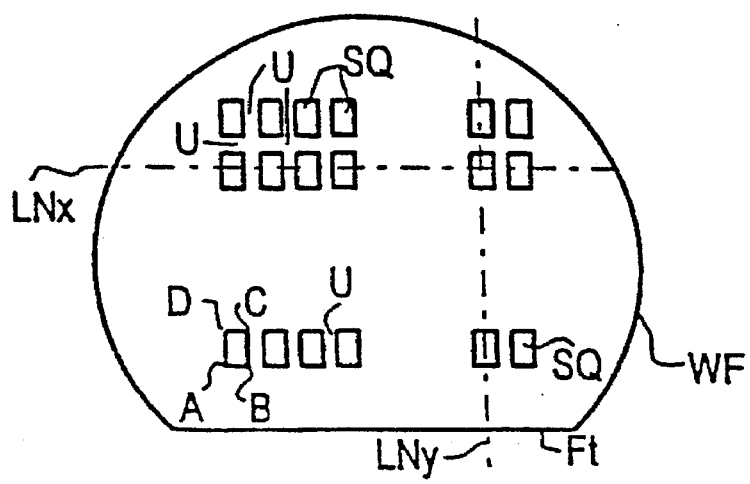
FIG. 5 is a side-elevational view of a wafer with a flat region.

Since semiconductor wafers WF often have a so-called flat Ft (in other words, a region on the intrinsically round semiconductor wafer WF is flattened) as is seen in FIG. 5, the assumption in the ensuing method will be that the semiconductor wafers WF to be checked have such a flat Ft. It is also assumed that semiconductor chips to be formed on the semiconductor wafers WF in the manufacturing process are rectangular, or optionally square, and are aligned parallel to the flat Ft.

It is assumed as well that the semiconductor chips to be made from the semiconductor wafer WF to be checked are integrated semiconductor memories which, regardless of their memory type (volatile memories such as DRAMs, SRAMs, and nonvolatile memories [NV memories] such as ROMs, PROMs, EEPROMs), are known to have large regions, seen in FIG. 5, of regular structures SQ (so-called memory cell blocks or memory cell fields), as well as regions of irregular structures which, for instance, contain so-called peripheral circuits, such as decoders and amplifiers, and connection surfaces (pads). The regions of regular structures SQ as a rule make up from 80 to 95% of the total memory chip. On such a semiconductor wafer WF, there are also regions (generally called scored frames) between the individual chips that are used to break apart the (finished) semiconductor wafer WF into a chip card or the like for the mounting of the individual chips in a housing. In the method, only those regions of the regular structures SQ are checked. In view of their large proportion of the entire surface area of the semiconductor wafer WF, this is entirely adequate.

Figure 4:
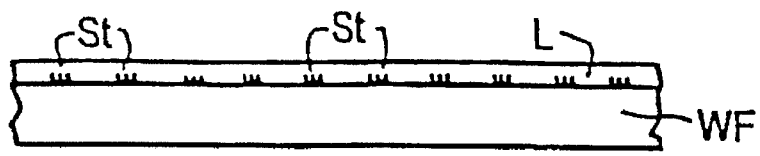
FIG. 4 is a fragmentary, side-elevational view of a wafer having structures and a lacquer layer.

Another prerequisite of the method is that a semiconductor wafer WF, as is shown in FIG. 4, have at least one layer that already contains structures St of the semiconductor chips to be completed, as well as a lacquer layer L (for additional structuring steps) as the top layer, and these layers need to be checked.

Automation by means of the apparatus of the invention offers the following advantages:

More measurement points can be checked in the same or even less measuring time (per wafer); that is the checking is more accurate.

Human mistakes (transposing the detection of good/reject and sorting in accordance with good/reject) are precluded.

At a short measuring time per wafer, the throughput, in other words the productivity per employee, increases.

The possibility moreover presents itself of having one employee handle a plurality of apparatuses according to the invention which automatically check semiconductor wafers WF, so that the productivity can be increased even further (higher productivity is well known to mean lower manufacturing costs, which is eminently important today for manufacturers of integrated circuits).

The method proceeds as follows:

The semiconductor wafer WF is illuminated directly by the lighting device Lt1, for instance with white light. The lacquer layer L applied to the semiconductor wafer WF reflects the light Lt.

Through the use of the camera CAM, which is disposed vertically above the semiconductor wafer WF and which "looks" at the semiconductor wafer because of this configuration, the degree of reflection, or reflectance, R of the reflected light Lt will be ascertained as follows (reflectance R is understood in this case to mean the measure of brightness, from the semiconductor wafer WF which strikes or acts upon the lens of the camera CAM):

First, through the use of the evaluation device PC, a first line LNx, which serves as a measurement line and extends parallel to and at a given distance from the flat Ft, is simulated, or in other words "imagined", on the surface of the lacquer L of the semiconductor wafer WF, as is seen in FIG. 5. The brightness of the semiconductor wafer WF, that is the value of the reflectance R, is ascertained by the camera CAM and the evaluation device PC along this imaginary line LNx at selected points Px ("pixels", which are not shown for the sake of simplicity) and buffer-stored together with a position value x of these points Px, in the evaluation device PC.

Figure 6:
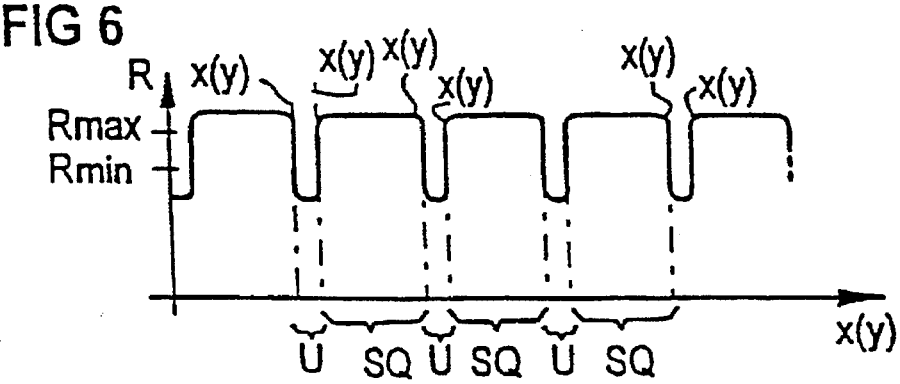
FIG. 6 is a diagram showing measured values of reflectance.

Referring to FIG. 6, if values for the ascertained and measured reflectance R that are below a predetermined minimum value Rmin are found along this imaginary line LNx multiple times, then the ascertained and buffer-stored data referring to this line LNx are discarded as unusable. It is assumed in fact that the line LNx does not extend predominantly through the large surfaces SQ of the regular structures but rather through the regions of irregular structures or through a scored frame. However, these regions and the scored frame (known as the "U" seen in FIG. 5) are not to be checked, by agreement. Instead of the imaginary line LNx which has been surveyed, a further "imaginary" line LNx1 is selected at a given distance from the imaginary line LNx and used (this is not shown in FIG. 5 for the sake of simplicity), and the reflectance R is also ascertained and buffer-stored with respect to the line LNx1, along with the associated position values x, as was done for the originally used imaginary line LNx.

If the values of the reflectance R of this further imaginary line LNx1 also have values below the minimum value Rmin multiple times, then the entire process of "discarding the data of this line LNx1, assumption of a further imaginary line LNx2, ascertainment and evaluation of the values of its reflectance R and of the associated position values x, and buffer-storing" is carried out once again as described above.

This is done overall often enough until an imaginary line LNx, LNx1, LNx2, ... has been found having values for the reflectance R which meet the criterion of the minimum value Rmin multiple times. If no such imaginary line LNx, LNx1, ... can be ascertained (optionally limited to a maximum number of attempts to find a suitable line LNx) that meets this criterion, then the check of this semiconductor wafer WF is discontinued, because it is assumed that either a defect of greater extent is involved, or the semiconductor wafer WF perhaps does not even have any structures St underneath the lacquer layer L.

In the case in which the search for an imaginary line LNx, ... that is located parallel to the flat Ft has lead to values for the reflectance R that meet the criterion of the minimum reflectance Rmin multiple times, then completely an accordance with the previous line, a new imaginary line LNy is simulated, somewhere over the semiconductor wafer WF to be checked, at right angles to the imaginary line that was found (it will be assumed below that this line which was found was the first imaginary line LNx), as is seen in FIG. 5. The values of the reflectance R of the reflected light Lt (together with the associated position values y) are again measured along this new imaginary line, at measurement points Py, by means of the camera and are buffer stored in the evaluation device PC. These values must again meet the criterion of the minimum reflectance Rmin multiple times (although it is conceivable that this reflectance may have a different value than for the imaginary line LNx parallel to the flat Ft). If the values do not meet that criterion, then the steps already described for the imaginary line LNx for finding an imaginary line LNx1, LNx2, ... are carried out analogously with respect to the new imaginary line LNy, with additional new imaginary lines LNy1, LNy2, etc. (each time at a given distance from the previously measured new imaginary line LNy, LNy1, etc.), until such time as it is either found (optionally after a predetermined maximum number of attempts) that no new imaginary line LNy, ... can be found which meets the criterion of the minimum reflectance Rmin (in which case checking of the affected semiconductor wafer WF is discontinued), or until such a line has been found (this will be assumed, for the purposes of the further description below, to be the original line LNy).

In the event that it has been possible to find a usable imaginary line LNx and LNy, then the position values x (for the imaginary line LNx) and y (for the imaginary line LNy) at the various measurement points of these lines LNx and LNy are already in buffer storage. The position values are referred to the location of the flats Ft. If at all possible, the measurement points Px and Py should be spaced so closely together that the boundaries between the various spaces of the regular structures SQ and the regions U (irregular structures and scored frames) are detected as accurately as possible (for instance, by way of their associated values for the reflectance R).

FIG. 6 shows an example of the course of the measured values of the reflectance R along the imaginary line LNx. The same is correspondingly true for the imaginary line LNy, as given by the letter "y" in parentheses on the abscissa. In the diagram, "SQ" stands for the (presumably rectangular) large surfaces of regular structures SQ, while "U" stands for the (smaller) regions of irregular structures and the various scored frames. The other designations "X", "Y" (in parentheses) that are also used will be explained later below. The drawing is based on the fact that the large surfaces of the regular structures SQ in the normal case have high values of the reflectance R, while the regions U have a usually markedly lower value for the reflectance R.

Figure 7:
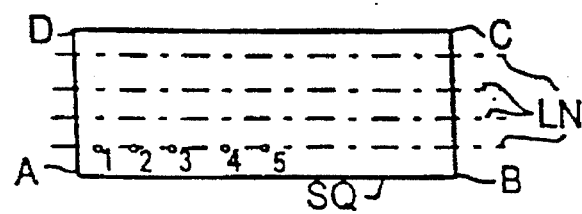
FIG. 7 is an enlarged view of a wafer having measuring lines.

In the case of the further method steps, that is for a semiconductor wafer WF for which imaginary lines LNx, LNy had been found that met the criterion of the minimum value Rmin, those points or in other words coordinates X, Y (see FIG. 6) that are of interest are those that are located at the periphery of the large surfaces of the regular structures SQ and the other regions U of irregular structures and the scored frames (that is, corner points A, B, C, D of the large surfaces of the regular structures SQ, as is shown in FIGS. 5 and 7), since the regions U are to be precluded from the check, by agreement. To that end, these coordinates X, Y are ascertained by means of the evaluation device PC from the position points x of one imaginary line LNx (or the further imaginary line LNx1 or LNx2, etc. being used as a substitute for it) and the position points y of the other imaginary line LNy (or the further imaginary line LNy1 or LNy2, etc. being used as a substitute for it) having associated values of the reflectance R, and the information that the surfaces of the regular structures SQ (that is, the memory cell fields) are rectangular.

The ascertainment is performed in a way which is easily carried out mathematically from the information that the large surfaces of the regular structures SQ form rectangles which repeat regularly in the x and y directions (that is, parallel and vertically to the flat Ft and thus parallel and vertically to the respective imaginary lines LNx, LNy) and from the evaluation criterion that only those position points x and y of the two imaginary lines LNx, LNy having an associated value of the reflectance R which exceeds a predetermined maximum value Rmax, that at the same time are neighboring points of position values x and y which fall below this maximum value Rmax, are taken into account. All of the position points x and y having an associated value of the reflectance R which is below this maximum value Rmax are considered to be regions that are not to be checked and are thus ignored in the remainder of the method.

Thus, with respect to the semiconductor wafer WF to be checked, all of the rectangular surfaces of the regular structures SQ (which may optionally be square, as a special case of a rectangle) within which the check is to be performed are defined. The regions U are by agreement precluded from the check. Incomplete surfaces of the regular structures SQ, which correspond to the incomplete peripheral chips of a semiconductor wafer WF, can also be precluded from the check.

The further method steps, which will be described below for a surface SQ, are employed successively on each individual rectangular surface SQ of the semiconductor wafer WF. They are again based on the principle of imaginary lines, but unlike the imaginary lines LNx, LNy described above they will be called measuring lines LN below.

In the case of each of the rectangular surfaces of the regular structures SQ to be checked (see FIG. 7), at least one measuring line LN is "drawn by imagination" parallel to one edge (four measuring lines LN are drawn parallel to the respective edges AB and CD in FIG. 7 by way of example), or in other words parallel to the longer edge.

Along each of these measuring lines LN the applicable value of the reflectance R is ascertained, by means of the camera CAM and the evaluation device PC, and buffer-stored for predetermined measurement points 1, 2, 3, . . . . The more measuring lines LN that are used per surface SQ, and the more such points 1, 2, 3, . . . that are given, the more accurate the checking becomes.

Figure 8:
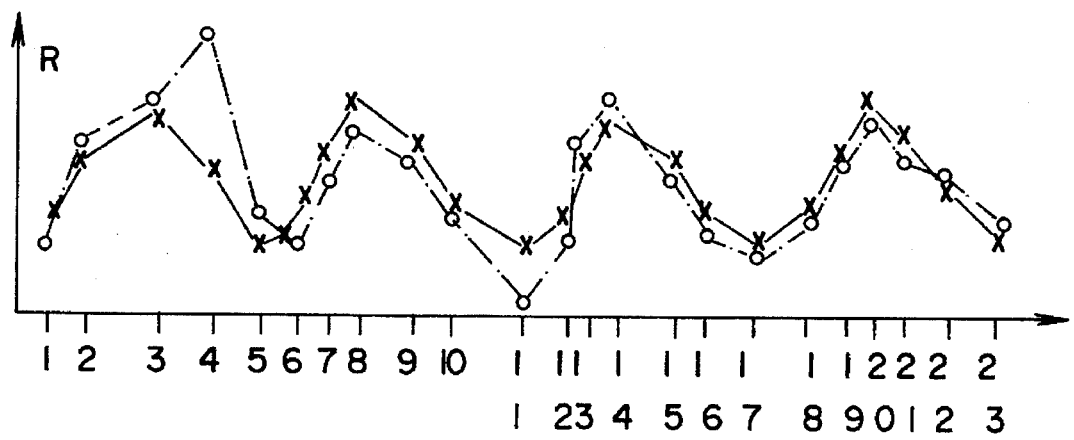
FIG. 8 is a diagram showing courses of the reflectance.

The two courses shown in FIG. 8 result, for example, in the case of the reflectance R along two selected measuring lines LN. Measurement points 1 to 23 are plotted on the abscissa. The applicable value of the reflectance R can be read off from the ordinate.

The values marked "x" of the reflectance R are values along a first measuring line LN. As the possible criteria to be described below for detecting whether or not a defect is present indicate, no defect can be found along this measuring line. Although various values of the reflectance R are present (caused by the various structures inside the surface of the regular structures SQ, under the lacquer layer L), nevertheless, as can be seen from the evaluation criteria given below, these values are within the range of the usual values to be expected, so that the surface of the regular structures SQ being checked with reference to this measuring line LN can be judged "good". The values of the reflectance R exhibit a periodic course. This is due to the fact that modern integrated semiconductors (one of which is of course to be made along with the present semiconductor wafer WF, and therefore by means of the surfaces of the regular structures SQ in question) have a plurality of memory cell fields disposed next to one another. Each period shown is accordingly equivalent to one such (future) memory cell field.

The values marked "o" for the reflectance R in FIG. 8 are measurement values along a second measuring line LN, for instance of the same surface of the regular structures SQ. The measurement points 4 and 11 are particularly striking.

The value of the reflectance R for the measurement point 4 (that is, within the first period) is markedly above the other measurement points, and especially with respect to the local maximum values thereof within each of the further periods 2, . . . . A defect is involved in this case, which is caused by a white particle. Since a white particle better reflects the light Lt than the other points of the lacquer layer L, this value is especially high.

The value of the reflectance R at the measurement point 11, which (coincidentally) is located at the transition from the second to the third period, is especially low as compared with the other measurement points, and especially as compared with the minimum values of the various periods. This can be ascribed to the fact that a dark particle is present at the affected point of the surface of the regular structures SQ, which is located between the second and third (yet to be made) memory cell field. However, it could also be that at this point the lacquer layer L is too thin or even has a hole in it. Thus, in the further production of the memory chip, structuring defects such as underetching, etc., could occur at this point. In any case, the measured values along the second measuring line LN indicate two defects, each individual one of which, upon being detected, causes the semiconductor wafer WF to be accordingly shunted elsewhere and possibly reworked.

With the aid of the measurement points 1, 2, . . . per measuring line LN, the evaluation device PC accordingly ascertains from evaluation criteria whether the rectangular surface of the regular structures SQ, and thus the entire semiconductor wafer WF being investigated, is OK or is defective. The results (optionally along with the geometrical data of where defects are located) can then be output by the evaluation device PC, for instance in the form of data on storage media (magnetic tapes, hard disk), by printout, or by triggering appropriate machines for post processing. Many kinds of possibilities are conceivable in this case.

The following evaluation criteria in particular can be used in determining whether the semiconductor wafer WF being checked, or its rectangular surfaces of the regular structures SQ, are or are not OK:

Either for each separate measuring line LN of a surface of the regular structures SQ, or for all of the measuring lines LN of the affected surface of the regular structures SQ, the maximum values of reflectance R of the individual periods that occur can be ascertained and thereupon checked as to whether or not they differ from one another by more than one predetermined allowable differential value. If so, a defect is assumed and the applicable value and the associated coordinates are buffer-stored and optionally output or further processed.

The same can be done for the corresponding minimal values of the reflectance R.

Once all of the rectangular surfaces of the regular structures SQ of the semiconductor wafers WF have been checked by means of the method described above, and corresponding statements have been made about the wafer WF being checked, this method is then ended.

Figure 2:
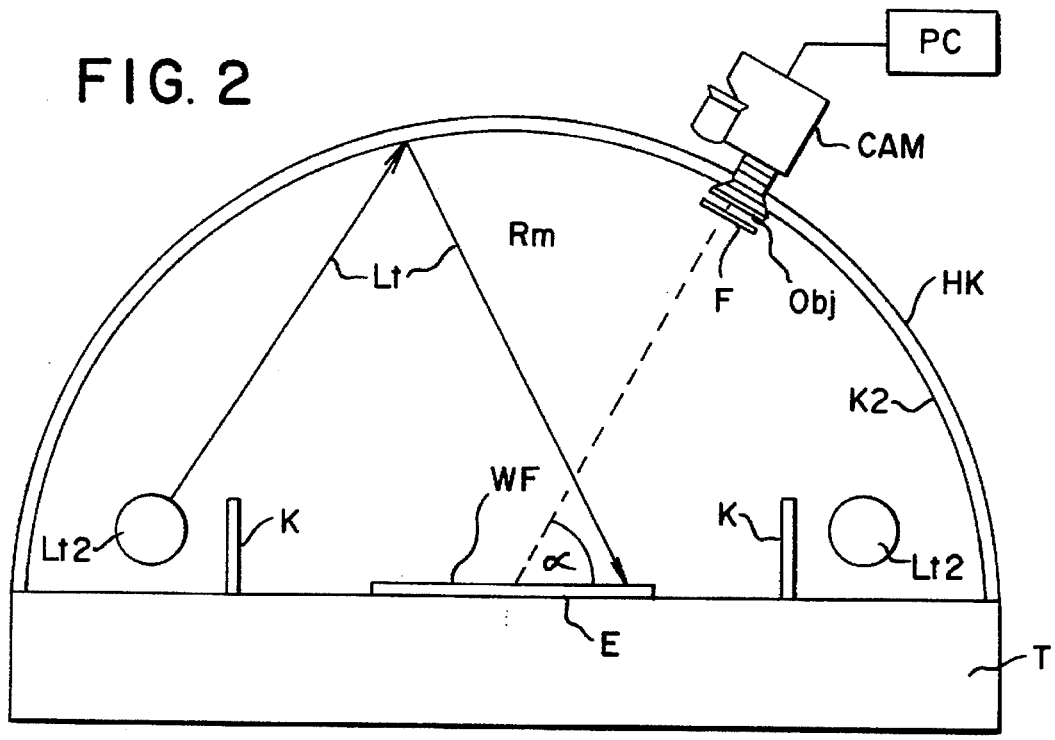

FIG. 2 shows a second embodiment of the apparatus of the invention. It is constructed similarly to the first embodiment but differs markedly from it in some points.

The second embodiment likewise has a device E for receiving the semiconductor wafer WF to be checked, and an illuminating device or light Lt2. The latter, however, serves to illuminate the semiconductor wafer WF indirectly. The hemispherical hood device HK that was already described is also present, but with a surface K2 in the interior that to a great extent reflects incident light Lt. It is therefore preferably white. A further hood device K that absorbs incident light Lt is also disposed between the lighting device Lt2 and the device E for receiving the semiconductor wafer WF to be checked, and this hood device is constructed in such a way that it prevents light from directly striking the device E and the semiconductor wafer WF. In other words, the semiconductor wafer WF can only be lighted indirectly with the lighting device Lt2, by reflection of the light Lt at the hemispherical hood device HK. A camera CAM is again disposed on the hemispherical hood HK in such a way that its lens Obj looks into the space Rm inside the hemispherical hood device HK. However, the camera CAM is not disposed vertically with respect to the center point of the device E for receiving the semiconductor wafer WF, as in the first embodiment of FIG. 1, but rather at an angle α hat is greater than 0° and less than 90°. An angular position of from 40° to 70° has proved good, with an optimal value being 60°. In this case, the camera can in fact reflect neither directly nor indirectly onto the semiconductor wafer WF, which would impede detection of the values of the reflectance R. It is also advantageous if the lens Obj of the camera CAM is equipped with a red filter F, which increases the contrast of the picture being taken.

The camera CAM, as in the first embodiment, is connected to an evaluation device PC, which serves to control the camera CAM and to receive, process, buffer-store and output the data or images transmitted by the camera CAM.

The following further features are advantageous in both embodiments of the apparatus (that is, in the apparatuses of FIGS. 1 and 2):

The light of the lighting devices Lt1 and Lt2 is white. The further hood devices K have a black surface. Further parts of the camera CAN, if any, which are located inside the hemispherical hood device HK, are disposed in such a way that they are concealed by the lens Obj when observed from the semiconductor wafer WF or the device E. It is also advantageous, for the sake of uniform illumination, if the lighting devices Lt1 and Lt2 and/or the further hoods K are annular. A bottom plate P1 is not absolutely necessary (except perhaps for mechanical reasons, reasons of stability, or for the sake of simpler processing of pictures being taken). However, if it is present, then it should be light-absorbent, and preferably black.

The second embodiment has the following advantage over the first embodiment: defects occur in semiconductor wafers WF that cannot be rendered visible and thus are detectable with a vertically positioned camera CAM and/or with direct illumination of the semiconductor wafer WF. However, with this second embodiment, that is by means of indirect lighting and an obliquely placed camera CAM, even these defects can be detected in most cases, so that reworking of the affected semiconductor wafers WF can be performed in good time, which in turn increases the yield of semiconductor memories to be made and therefore lowers production costs overall.

Figure 3:
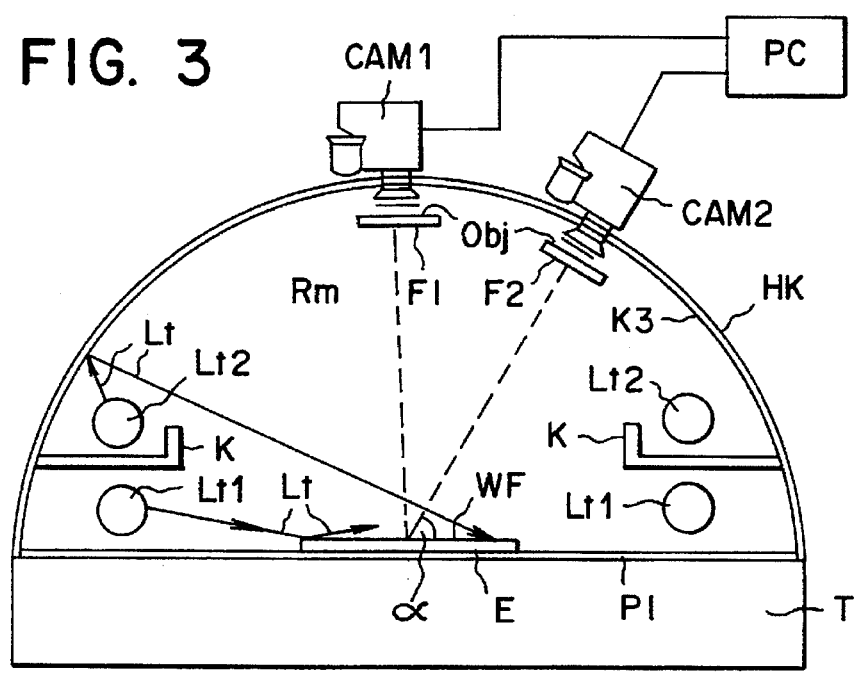

A third embodiment of the apparatus, which is shown in FIG. 3, combines the advantages of the first two embodiments, namely the detection of defects both with a vertically positioned camera CAM1 in direct lighting and with an obliquely positioned camera CAM2 in indirect lighting. The embodiment will be described below in conjunction with FIG. 3.

Once again, the apparatus has a device E for receiving the semiconductor wafer WF to be checked. It has two lighting devices Lt1, Lt2, of which the first lighting device Lt1 serves to provide direct lighting of the semiconductor wafer WF with a first color Gn that is preferably green, and the second lighting device Lt2 serves to provide indirect lighting of the semiconductor wafer WF with a second color Rt that is complementary to the first color Gn. The second color Rt is preferably red. A hemispherical hood device HK, which is once again a component of this third apparatus, has a surface K3 in the interior Rm, which is likewise that of the second color Rt or in other words is preferably red. The hemispherical hood HK forms a largely closed interior Rm, by means of a bottom plate P1 which, however, is not absolutely necessary. This bottom plate P1 may have the second color Rt, that is, preferably red, on its surface facing toward the space Rm. However, according to another feature, the surface may also be black. Above the first lighting device Lt1 is a further hood device K, which is opaque. The further hood device K is constructed in such a way that on one hand the semiconductor wafer WF can be lighted directly by means of the first lighting device Lt1, and on the other hand this semiconductor wafer WF can only be lighted indirectly by the second lighting device Lt2.

Vertically above the center point of the device E for receiving the semiconductor wafer WF, the first camera CAM1 is disposed on the hemispherical hood device HK in such a way that its lens Obj looks into the space Rm inside the hemispherical hood device HK, and looks at the device E in that space. The first camera CAM1 has a filter F1, which admits only light of the first color Gn, or in other words preferably green light (that is, it is a green filter).

The camera CAM2 is also disposed on the hemispherical hood device HK in such a way that its lens Obj looks into the space Rm inside the hemispherical hood device HK and looks at the device E. The second camera CAM2 also has a filter F2, but it admits only light of the second color Rt, that is preferably red light (in other words, it is a red filter).

With respect to the center point of the device E, the second camera CAM 2 is disposed at an angle α that is larger than 0° and at maximum is large enough to ensure that the second camera CAM2 does not come into contact with the first camera CAM1.

Both cameras CAM1, CAM2 are connected to an evaluation device PC, which serves to control the cameras CAM1, CAM2 as well as to detect, buffer-store, further process and output data or images obtained from the cameras CAM1, CAM2.

In order to ensure that during operation the two different types of lighting (direct and indirect lighting) with their light conditions, including reflections that occur or that are to be suppressed, will influence one another as little as possible, at the hemispherical hood device HK, the system has been chosen to have the mutually complementary colors Gn, Rt of the lighting devices Lt1, Lt2 and the correspondingly constructed surfaces of both the hood device HK and the bottom plate P1.

It is also advantageous if parts of the cameras CAM1 and/or CAM2 located in the space Rm inside the hemispherical hood device HK, for one of the two cameras CAM1, CAM2 or both cameras CAM1, CAM2, are disposed in such a way that they are concealed by the lens Obj of the respective camera CAM1, CAM2, as viewed from the semiconductor wafer WF or from the device E.

It is additionally advantageous if at least one of the two lighting devices Lt1, Lt2 and/or the further hood device K is annular or is disposed annularly.

The device E for receiving the semiconductor wafers WF may also be advantageously constructed in various ways: it may be constructed as a component of the bottom plate P1, it may be disposed on the bottom plate P1, or it may be let into the bottom plate P1.

It is likewise advantageous (in terms of the second apparatus) if the angle α, at which the second camera CAM2 is disposed relative to the center point of the device E, is from 40° to 70°. A configuration of 60° is optimal.

We claim:

1. An apparatus for checking semiconductor wafers, comprising:

a receiver for a semiconductor wafer to be checked, said receiver having a center point;

a first light for directly illuminating the semiconductor wafer with light of a first color;

a second light for indirectly illuminating the semiconductor wafer with light of a second color being complementary to the first color;

a hemispherical hood having a surface of the second color and having a hemispherical region defining an interior inside said hemispherical region;

a further hood being disposed above said first light, being opaque to incident light, permitting the semiconductor wafer to be illuminated directly by said first light, and permitting the semiconductor wafer to only be illuminated indirectly by said second light;

a first camera disposed at said hemispherical hood vertically above said center point of said receiver for the semiconductor wafer to be checked, said first camera having a lens looking into said interior and a filter admitting only light of the first color;

a second camera being disposed at said hemispherical hood and having a lens looking into said interior and a filter admitting only light of the second color, said second camera being disposed at an angle greater than 0° relative to said center point of said receiver for the semiconductor wafer to be checked; and an evaluator being connected to both of said cameras for controlling said cameras and for receiving, buffer-storing, further processing and outputing data transmitted from said cameras.

2. The apparatus according to claim 1, wherein said further hood has a black surface.

3. The apparatus according to claim 1, wherein at least one of said cameras has further parts being disposed in said interior inside said hemispherical hood and being concealed by said lens, as viewed from the semiconductor wafer.

4. The apparatus according to claim 1, wherein at least one of said lights is annular.

5. The apparatus according to claim 1, wherein said further hood is disposed annularly.

6. The apparatus according to claim 1, including a bottom plate largely closing off said interior at said receiver for the semiconductor wafer to be checked.

7. The apparatus according to claim 6, wherein said receiver for the semiconductor wafer to be checked is a component of said bottom plate.

8. The apparatus according to claim 6, wherein said receiver for the semiconductor wafer is disposed on or let into said bottom plate.

9. The apparatus according to claim 1, wherein said angle at which said second camera is disposed is from 40° to 70° and preferably 60°.

10. The apparatus according to claim 1, wherein the first color is green.

11. The apparatus according to claim 1, wherein the second color is red.

* * * * *